(12) United States Patent
Hosoi et al.

(10) Patent No.: US 12,205,704 B2
(45) Date of Patent: Jan. 21, 2025

(54) APPARATUS, SYSTEM, METHOD, AND COMPUTER READABLE MEDIUM FOR REHABILITATION PLANNING USING MACHINE LEARNING

(71) Applicant: NEC Corporation, Tokyo (JP)

(72) Inventors: Toshinori Hosoi, Tokyo (JP); Yuki Kosaka, Tokyo (JP); Masahiro Kubo, Tokyo (JP); Yuan Luo, Tokyo (JP)

(73) Assignee: NEC CORPORATION, Tokyo (JP)

( * ) Notice: Subject to any disclaimer, the term of this patent is extended or adjusted under 35 U.S.C. 154(b) by 348 days.

(21) Appl. No.: 17/761,288

(22) PCT Filed: Jul. 29, 2020

(86) PCT No.: PCT/JP2020/029111
§ 371 (c)(1),
(2) Date: Mar. 17, 2022

(87) PCT Pub. No.: WO2021/065184
PCT Pub. Date: Apr. 8, 2021

(65) Prior Publication Data
US 2022/0375568 A1    Nov. 24, 2022

(30) Foreign Application Priority Data
Oct. 4, 2019  (JP) ................. 2019-184153

(51) Int. Cl.
*G16H 20/30* (2018.01)
*G16H 10/60* (2018.01)

(52) U.S. Cl.
CPC ............. *G16H 20/30* (2018.01); *G16H 10/60* (2018.01)

(58) Field of Classification Search
None
See application file for complete search history.

(56) References Cited

U.S. PATENT DOCUMENTS 6,656,091 B1 * 12/2003 Abelbeck ........... A63B 24/0062
                                                            482/8
9,314,190 B1 *  4/2016 Giuffrida ........... A61N 1/36003
(Continued)

FOREIGN PATENT DOCUMENTS

JP    2011-243203 A    12/2011
JP    2014-127057 A     7/2014
(Continued)

OTHER PUBLICATIONS

International Search Report for PCT Application No. PCT/JP2020/029111, mailed on Nov. 2, 2020.

*Primary Examiner* — John A Pauls

(57) ABSTRACT

A rehabilitation planning apparatus, a rehabilitation planning system, a rehabilitation planning method, and a program capable of efficiently creating a rehabilitation plan are provided. A rehabilitation planning apparatus (1) includes a rehabilitation pattern selection unit (2), an ability value prediction unit (3) that predicts a physical ability value after a target patient performs rehabilitation indicated in a selected rehabilitation pattern, a repetition control unit (4) that performs control so that the selection by the rehabilitation pattern selection unit (2) and the prediction by the ability value prediction unit (3) are repeated, and a determination unit (5) that determines a rehabilitation pattern for, among combinations of rehabilitation patterns and physical ability values obtained through the repetition of the selection and the prediction, a combination of which the physical ability value satisfies a predetermined condition as a rehabilitation plan for the target patient.

10 Claims, 11 Drawing Sheets

(56) References Cited

U.S. PATENT DOCUMENTS

| | | | |
|---|---|---|---|
| 10,271,768 B1* | 4/2019 | Murali | A61B 5/11 |
| 2005/0090372 A1 | 4/2005 | Burrows et al. | |
| 2006/0264786 A1* | 11/2006 | Nashner | A61B 5/4023 |
| | | | 600/595 |
| 2010/0016730 A1* | 1/2010 | Tanaka | A61B 3/024 |
| | | | 600/476 |
| 2013/0203031 A1* | 8/2013 | Mckinnon | G09B 23/28 |
| | | | 434/262 |
| 2013/0232103 A1* | 9/2013 | Saeed | G16H 50/20 |
| | | | 706/46 |
| 2017/0140109 A1* | 5/2017 | Kheifetz | G16H 50/50 |
| 2019/0216368 A1* | 7/2019 | Chen | G16H 50/30 |
| 2022/0328187 A1* | 10/2022 | Kosaka | G16H 50/20 |

FOREIGN PATENT DOCUMENTS

| | | |
|---|---|---|
| JP | 2016-197330 A | 11/2016 |
| WO | 2005/003902 A2 | 1/2005 |
| WO | 2019/008657 A1 | 1/2019 |

\* cited by examiner

| TIME OF PERFORMANCE | REHABILITATION MENU |
|---|---|
| FIRST WEEK | [SUPERORDINATE TASK] XXXX<br>[SUBORDINATE TASK] YYYY<br>[PROGRAM] PERFORM EXERCISE A FOR BODY PART A IN POSTURE A |
| | [SUPERORDINATE TASK] XXXX<br>[SUBORDINATE TASK] YYYY<br>[PROGRAM] PERFORM EXERCISE B FOR BODY PART B IN POSTURE B |
| SECOND WEEK | [SUPERORDINATE TASK] XXXX<br>[SUBORDINATE TASK] YYYY<br>[PROGRAM] PERFORM EXERCISE C FOR BODY PART C IN POSTURE C |
| THIRD WEEK | [SUPERORDINATE TASK] XXXX<br>[SUBORDINATE TASK] YYYY<br>[PROGRAM] PERFORM EXERCISE A FOR BODY PART A IN POSTURE A |
| | [SUPERORDINATE TASK] XXXX<br>[SUBORDINATE TASK] YYYY<br>[PROGRAM] PERFORM EXERCISE C FOR BODY PART C IN POSTURE C |
| | [SUPERORDINATE TASK] XXXX<br>[SUBORDINATE TASK] YYYY<br>[PROGRAM] PERFORM EXERCISE D FOR BODY PART D IN POSTURE D |
| FOURTH WEEK | [SUPERORDINATE TASK] XXXX<br>[SUBORDINATE TASK] YYYY<br>[PROGRAM] PERFORM EXERCISE B FOR BODY PART B IN POSTURE B |
| | [SUPERORDINATE TASK] XXXX<br>[SUBORDINATE TASK] YYYY<br>[PROGRAM] PERFORM EXERCISE C FOR BODY PART C IN POSTURE C |
| | [SUPERORDINATE TASK] XXXX<br>[SUBORDINATE TASK] YYYY<br>[PROGRAM] PERFORM EXERCISE E FOR BODY PART E IN POSTURE E |

| TIME OF PERFORMANCE | REHABILITATION MENU | TYPE OF ABILITY |||||
|---|---|---|---|---|---|---|
| | | MEAL | DRESSING | BATHING | ... | MEMORY |
| FIRST WEEK | [PROGRAM] PERFORM EXERCISE A FOR BODY PART A IN POSTURE A [SUPERORDINATE TASK] XXXX [SUBORDINATE TASK] YYYY | | ← | | | |
| | [PROGRAM] PERFORM EXERCISE B FOR BODY PART B IN POSTURE B [SUPERORDINATE TASK] XXXX [SUBORDINATE TASK] YYYY | ← | | | | |
| SECOND WEEK | [PROGRAM] PERFORM EXERCISE C FOR BODY PART C IN POSTURE C [SUPERORDINATE TASK] XXXX [SUBORDINATE TASK] YYYY | | ← | | | |
| | [PROGRAM] PERFORM EXERCISE A FOR BODY PART A IN POSTURE A [SUPERORDINATE TASK] XXXX [SUBORDINATE TASK] YYYY | | ← | | | |
| THIRD WEEK | [PROGRAM] PERFORM EXERCISE C FOR BODY PART C IN POSTURE C [SUPERORDINATE TASK] XXXX [SUBORDINATE TASK] YYYY | | | ← | | |
| | [PROGRAM] PERFORM EXERCISE D FOR BODY PART D IN POSTURE D [SUPERORDINATE TASK] XXXX [SUBORDINATE TASK] YYYY | | | ← | | |
| | [PROGRAM] PERFORM EXERCISE B FOR BODY PART B IN POSTURE B [SUPERORDINATE TASK] XXXX [SUBORDINATE TASK] YYYY | ← | | | | |
| FOURTH WEEK | [PROGRAM] PERFORM EXERCISE C FOR BODY PART C IN POSTURE C [SUPERORDINATE TASK] XXXX [SUBORDINATE TASK] YYYY | | | ← | | |
| | [PROGRAM] PERFORM EXERCISE E FOR BODY PART E IN POSTURE E [SUPERORDINATE TASK] XXXX [SUBORDINATE TASK] YYYY | ← | | | | |

APPARATUS, SYSTEM, METHOD, AND COMPUTER READABLE MEDIUM FOR REHABILITATION PLANNING USING MACHINE LEARNING

This application is a National Stage Entry of PCT/JP2020/029111 filed on Jul. 29, 2020, which claims priority from Japanese Patent Application 2019-184153 filed on Oct. 4, 2019, the contents of all of which are incorporated herein by reference, in their entirety.

TECHNICAL FIELD

The present invention relates to a rehabilitation planning apparatus, a rehabilitation planning system, a rehabilitation planning method, and a program.

BACKGROUND ART

Patent Literature 1 discloses an information processing apparatus that supports rehabilitation (e.g., a rehabilitation training or a rehabilitation therapy). This information processing apparatus includes an estimation unit that estimates recovery transition information based on movement information of a certain rehabilitation target person corresponding to movement information of a user and movement evaluation information thereof, and a selection unit that selects movement information that will be used as a target for the user based on the estimated recovery transition information.

In recent years, there has been a need for a technology for supporting rehabilitation as described above, and research and development for such technology has been pursued. In general, a patient performs rehabilitation according to a rehabilitation plan prepared in advance.

CITATION LIST

Patent Literature

Patent Literature 1: International Patent Publication No. WO2019/008657

SUMMARY OF INVENTION

Technical Problem

In general, a rehabilitation plan is created by a therapist such as a physical therapist after some deliberation. However, in such a case, the person who has created the rehabilitation plan needs to examine the plan based on his/her experiences and intuitions, and advice from other therapists. Therefore, it takes time to examine the rehabilitation plan.

One of the objects to be attained by example embodiments disclosed in this specification is to provide a rehabilitation planning apparatus, a rehabilitation planning system, a rehabilitation planning method, and a program capable of efficiently creating a rehabilitation plan.

Solution to Problem

A rehabilitation planning apparatus according to a first aspect of the present disclosure includes:
rehabilitation pattern selection means for selecting one of a plurality of rehabilitation pattern candidates;
ability value prediction means for predicting a physical ability value after a target patient performs rehabilitation indicated in the selected rehabilitation pattern based on the selected rehabilitation pattern and target patient information by using a prediction model, the target patient information being information about the target patient;
repetition control means for controlling a repetition of a selection of a different rehabilitation pattern by the rehabilitation pattern selection means and a prediction corresponding to this rehabilitation pattern by the ability value prediction means; and
determination means for determining a rehabilitation pattern for, among combinations of rehabilitation patterns and physical ability values obtained through the repetition of the selection by the rehabilitation pattern selection means and the prediction by the ability value prediction means, a combination of which the physical ability value satisfies a predetermined condition as a rehabilitation plan for the target patient, in which
the prediction model is a model that has undergone a learning process in advance by using a plurality of pieces of past information and rehabilitation histories, each of the plurality of pieces of past information being information about a respective one of a plurality of past patients who performed rehabilitation in a past, and the rehabilitation histories being rehabilitation histories of the past patients associated with the pieces of past information.

A rehabilitation planning system according to a second aspect of the present disclosure includes a rehabilitation planning apparatus, and a terminal device, in which
the rehabilitation planning apparatus includes:
rehabilitation pattern selection means for selecting one of a plurality of rehabilitation pattern candidates;
ability value prediction means for predicting a physical ability value after a target patient performs rehabilitation indicated in the selected rehabilitation pattern based on the selected rehabilitation pattern and target patient information by using a prediction model, the target patient information being information about the target patient input from the terminal device;
repetition control means for controlling a repetition of a selection of a different rehabilitation pattern by the rehabilitation pattern selection means and a prediction corresponding to this rehabilitation pattern by the ability value prediction means; and
output control means for preforming control so as to output a rehabilitation pattern for, among combinations of rehabilitation patterns and physical ability values obtained through the repetition of the selection by the rehabilitation pattern selection means and the prediction by the ability value prediction means, a combination of which the physical ability value satisfies a predetermined condition as a rehabilitation plan for the target patient to the terminal device, and
the prediction model is a model that has undergone a learning process in advance by using a plurality of pieces of past information and rehabilitation histories, each of the plurality of pieces of past information being information about a respective one of a plurality of past patients who performed rehabilitation in a past, and the rehabilitation histories being rehabilitation histories of the past patients associated with the pieces of past information.

A rehabilitation planning method according to a third aspect of the present disclosure includes:
selecting one of a plurality of rehabilitation pattern candidates;

predicting a physical ability value after a target patient performs rehabilitation indicated in the selected rehabilitation pattern based on the selected rehabilitation pattern and target patient information by using a prediction model, the target patient information being information about the target patient;

controlling a repetition of a selection of a different rehabilitation pattern and a prediction corresponding to this rehabilitation pattern; and determining a rehabilitation pattern for, among combinations of rehabilitation patterns and physical ability values obtained through the repetition of the selection and the prediction, a combination of which the physical ability value satisfies a predetermined condition as a rehabilitation plan for the target patient, in which the prediction model is a model that has undergone a learning process in advance by using a plurality of pieces of past information and rehabilitation histories, each of the plurality of pieces of past information being information about a respective one of a plurality of past patients who performed rehabilitation in a past, and the rehabilitation histories being rehabilitation histories of the past patients associated with the pieces of past information.

A program according to a fourth aspect of the present disclosure causes a computer to perform:

a rehabilitation pattern selection step for selecting one of a plurality of rehabilitation pattern candidates;

an ability value prediction step of predicting a physical ability value after a target patient performs rehabilitation indicated in the selected rehabilitation pattern based on the selected rehabilitation pattern and target patient information by using a prediction model, the target patient information being information about the target patient;

a repetition control step of controlling a repetition of a selection of a different rehabilitation pattern and a prediction corresponding to this rehabilitation pattern; and a determination step of determining a rehabilitation pattern for, among combinations of rehabilitation patterns and physical ability values obtained through the repetition of the selection in the rehabilitation pattern selection step and the prediction in the ability value prediction step, a combination of which the physical ability value satisfies a predetermined condition as a rehabilitation plan for the target patient, in which the prediction model is a model that has undergone a learning process in advance by using a plurality of pieces of past information and rehabilitation histories, each of the plurality of pieces of past information being information about a respective one of a plurality of past patients who performed rehabilitation in a past, and the rehabilitation histories being rehabilitation histories of the past patients associated with the pieces of past information.

Advantageous Effects of Invention

According to the present disclosure, it is possible to provide a rehabilitation planning apparatus, a rehabilitation planning system, a rehabilitation planning method, and a program capable of efficiently creating a rehabilitation plan.

BRIEF DESCRIPTION OF DRAWINGS

FIG. 3 is a schematic diagram showing an example of a rehabilitation plan displayed on a terminal device under the control of an output control unit;

FIG. 4 is a schematic diagram showing an example of a rehabilitation plan displayed on a terminal device under the control of an output control unit;

DESCRIPTION OF EMBODIMENTS

Overview of Example Embodiment

Figure 1:
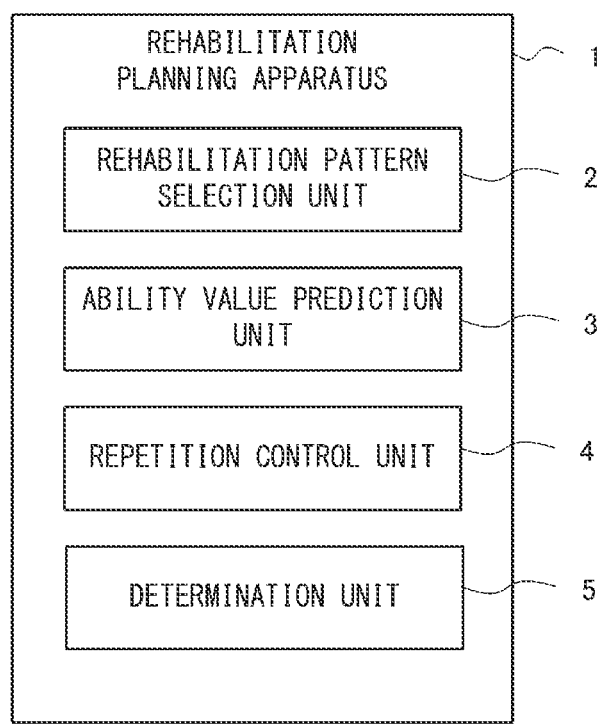
FIG. 1 is a block diagram showing an example of a configuration of a rehabilitation planning apparatus according to an outline of an example embodiment.

Prior to describing an example embodiment in detail, an outline of the example embodiment will be described. FIG. 1 is a block diagram showing an example of a configuration of a rehabilitation planning apparatus 1 according to an outline of an example embodiment. As shown in FIG. 1, the rehabilitation planning apparatus 1 includes a rehabilitation pattern selection unit 2, an ability value prediction unit 3, a repetition control unit 4, and a determination unit 5.

The rehabilitation pattern selection unit 2 selects one of a plurality of rehabilitation pattern candidates. Note that the rehabilitation pattern selection unit 2 selects different rehabilitation patterns in repeated selections. Note that the rehabilitation pattern is information representing a combination of contents of rehabilitation performed at predetermined intervals (e.g., on a weekly basis). Note that this combination does not necessarily have to be a combination of contents of rehabilitation performed over a plurality of predetermined periods, and instead may be a content of rehabilitation performed in one predetermined period. That is, the rehabilitation pattern is information representing a combination of contents of rehabilitation performed in m predetermined periods (m is an integer equal to or greater than one).

The ability value prediction unit 3 predicts a physical ability value after a target patient performs rehabilitation indicated in the rehabilitation pattern selected by the rehabilitation pattern selection unit 2. The ability value prediction unit 3 predicts a physical ability value after the target patient performs rehabilitation indicated in the selected rehabilitation pattern based on the selected rehabilitation pattern and target patient information, which is information about the target patient, by using a prediction model. In other words, the ability value prediction unit 3 predicts a physical ability value by inputting the rehabilitation pattern selected by the rehabilitation pattern selection unit 2 and the target patient information, which is information about the target patient, into the prediction model. Note that the target patient is a patient who is scheduled to perform rehabilitation according to a rehabilitation plan to be created. The prediction model is a model that has undergone a learning process in advance by using a plurality of pieces of past information, each of which is information about a respective one of a plurality of past patients, and rehabilitation histories of past patients associated with the pieces of past information. Note that the past patient is a patient who is different from the target patient and performed rehabilitation in the past.

The past information is a set of pieces of information about the past patients, and the target patient information is a set of pieces of information about the target patient. More specifically, the past information is a set of pieces of information representing features of the past patients, and the target patient information is a set of pieces of information representing features of the target patient.

Note that at least some of the items in the past information (types of information included in the past information) correspond to some of the items in the target patient information (types of information included in the target patient information). Further, rehabilitation histories of the past patients are associated with the past information.

The repetition control unit 4 controls repetitions of selections of different rehabilitation patterns by the rehabilitation pattern selection unit 2 and predictions corresponding to the rehabilitation patterns by the ability value prediction unit 3. The repetition control unit 4 controls the repetitions of selections by the rehabilitation pattern selection unit 2 and predictions by the ability value prediction unit 3 until an end condition is satisfied.

The determination unit 5 determines a rehabilitation pattern for, among combinations of rehabilitation patterns and physical ability values obtained through the above-described repetitions of selections and predictions, a combination of which the physical ability value satisfies a predetermined condition as a rehabilitation plan for the target patient. Note that the determination unit 5 may perform control so as to output the determined rehabilitation plan for the target patient.

As described above, according to the rehabilitation planning apparatus 1, a rehabilitation pattern by which a physical ability value will satisfy a predetermined condition after performing rehabilitation is found through repetitions of selections by the rehabilitation pattern selection unit 2 and predictions by the ability value prediction unit 3. Then, such a rehabilitation pattern is determined to be a rehabilitation plan for the target patient. Therefore, a therapist can create a rehabilitation plan for the target patient by referring to the determined rehabilitation plan. Alternatively, the therapist can determine the determined rehabilitation plan itself as the rehabilitation plan for the target patient. As described above, according to the rehabilitation planning apparatus 1, it is possible to provide useful information for examining a rehabilitation plan, and thereby to efficiently create the rehabilitation plan.

First Example Embodiment

Figure 2:
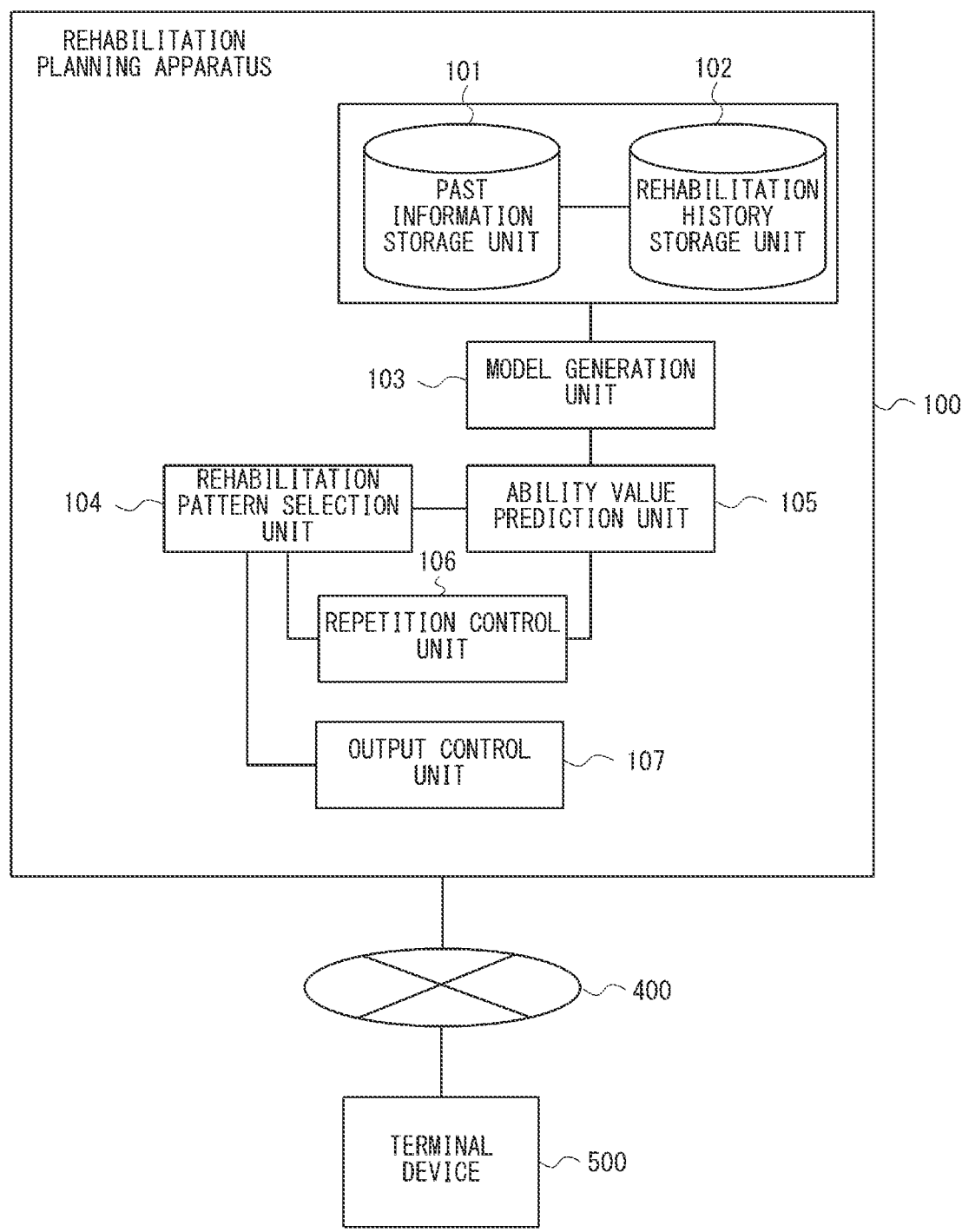
FIG. 2 is a block diagram showing an example of a configuration of a rehabilitation planning system according to a first example embodiment.

An example embodiment according to the present invention will be described hereinafter with reference to the drawings. FIG. 2 is a block diagram showing an example of a configuration of a rehabilitation planning system 10 according to a first example embodiment. The rehabilitation planning system 10 includes a rehabilitation planning apparatus 100 and a terminal device 500, and they are connected to each other through a network 400 wirelessly or through a cable so that they can communicate with each other.

The rehabilitation planning apparatus 100 is configured, for example, as a server. Further, the terminal device 500 is an arbitrary terminal such as a personal computer, a tablet-type terminal, or a smartphone. The terminal device 500 is equipped with an input device and an output device, and hence is able to receive information to be transmitted to the rehabilitation planning apparatus 100 and output (display) information received from the rehabilitation planning apparatus 100.

Note that although only one terminal device 500 is shown in FIG. 2, the rehabilitation planning system 10 may include a plurality of terminal devices 500.

As shown in FIG. 2, the rehabilitation planning apparatus 100 includes a past information storage unit 101, a rehabilitation history storage unit 102, a model generation unit 103, a rehabilitation pattern selection unit 104, an ability value prediction unit 105, a repetition control unit 106, and an output control unit 107. The rehabilitation planning apparatus 100 is an apparatus for assisting a therapist or the like to create a rehabilitation plan for a target patient. This rehabilitation plan is information indicating a schedule of rehabilitation that the target patient, who is a patient in a certain facility (or an institution), will perform. In this example embodiment, the above-described certain facility is, for example, but not limited to, a convalescent rehabilitation hospital to which patients who are transferred from an acute-phase hospital are admitted.

In the past information storage unit 101, past information for each past patient is stored. Information about each item in the past information and information about each item in the target patient information (which will described later) are, for example, expressed by numerical codes. Note that, when a model is generated (which will be described later), the past information used in the processing performed in the rehabilitation planning apparatus 100 preferably does not include past information about unusual patients (e.g., patients having special circumstances) because such information may disturb the generation of an appropriate model.

In the rehabilitation history storage unit 102, a rehabilitation history of each past patient is stored. For each past patient, the past information stored in the past information storage unit 101 and the rehabilitation history stored in the rehabilitation history storage unit 102 are associated with each other.

Note that although the past information storage unit 101 and the rehabilitation history storage unit 102 are shown as separate components in the example shown in FIG. 2, they may be implemented (i.e., constructed) as a one storage unit. Further, although the rehabilitation planning apparatus 100 includes the past information storage unit 101 and the rehabilitation history storage unit 102 in this example embodiment, the past information storage unit 101 and the rehabilitation history storage unit 102 may be implemented by an external apparatus(es). In such a case, the rehabilitation planning apparatus 100 may acquire the past information and the rehabilitation history from this external apparatus.

In this example embodiment, the past information includes patient's attributes, the name of a disease, symptoms, physical ability values, and an individual target. However, these information items are merely examples, and the past information is not limited to them. Specifically, the patient's attributes include, for example, any attribute information such as the age, the gender, and social information of the patient. Note that the social information is information representing the social states of the patient, and includes a family structure, the presence/absence of a roommate(s), the place of residence, the type of the building of the home (e.g., whether the building is a condominium or a two-story detached house), information about patient's medical insurance, and information about patient's nursing-care insurance.

The physical ability values are physical ability values related to patient's activities in daily life, and for example, physical ability values related to ADL (Activities of Daily Living) or IADL (Instrumental Activities of Daily Living). In this example embodiment, the physical ability values included in the past information are, specifically, evaluation scores in respective evaluation items included in an FIM (Function Independence Measure). However, other types of physical ability values may also be used.

In this example embodiment, the physical ability values included in the past information are information (e.g., time-series data) indicating temporal changes in the evaluation values in respective evaluation items in the FIM. That is, the past information includes histories of physical ability values. In this example embodiment, the histories of physical ability values include histories of physical ability values in rehabilitation (convalescent rehabilitation) performed in a convalescent rehabilitation hospital. They include physical ability values of the past patient before performing rehabilitation indicated in a rehabilitation history associated with the past information (a rehabilitation history stored in the rehabilitation history storage unit 102) and physical ability values after performing the rehabilitation. Further, in this example embodiment, the past information includes, as the histories of physical ability values, not only histories of physical ability values in convalescent rehabilitation, but also histories of physical ability values in rehabilitation performed in an acute-phase hospital (i.e., acute-phase rehabilitation). Although the physical ability values are respective values for a plurality of types of abilities (values in respective items in the FIM) in this example embodiment, they can also be physical ability values for one type of ability.

The individual target is information indicating an individual target of a patient in rehabilitation. For example, the individual target may be, but is not limited to, any of the below-shown items.

"Be able to cross a street within a time during which a traffic light is green", "Be able to walk at a quick pace"
"Be able to be reinstated as a clerical worker"
"Be able to live alone without nursing care"
"A score in each classification item in ADL-related indices such as the FIM becomes better than a predetermined value"
"A level of required support or a level of required care in the nursing-care field becomes better than a predetermined value"
"Be able to cross a street within a time during which a traffic light is green"
"Be able to be reinstated as a clerical worker who mainly operates a desk-top calculator"
"No assistance is required, except for bathing, and be able to live alone in his/her house as long as he/she receives a certain nursing-care service"
"Be able to walk while avoiding obstacles without feeling of wrongness as being observed by people around him/her"
"Be able to go up and down stairs while holding a light object in his/her house".

Each of the rehabilitation histories stored in the rehabilitation history storage unit 102 is information (time-series data) representing a combination of contents of rehabilitation that a past patient has actually performed at predetermined intervals (e.g., on a weekly basis). That is, the rehabilitation histories correspond to the above-described rehabilitation patterns. Note that this combination also does not necessarily have to be a combination of contents of rehabilitation performed over a plurality of predetermined periods, and instead may be a content of rehabilitation performed in one predetermined period. That is, the rehabilitation history is information representing a combination of contents of rehabilitation performed in m predetermined periods (m is an integer equal to or greater than one). The contents of rehabilitation include, for example, tasks that the patient desires to accomplish through the rehabilitation and contents (programs) of practices for accomplishing the tasks. Regarding the tasks, a superordinate task(s) and a subordinate task(s) may be set. Further, the rehabilitation history may also include various information items such as identification information of the therapist who performed the rehabilitation therapy and a place where the rehabilitation is performed. In this example embodiment, the rehabilitation history storage unit 102 specifically stores, as a rehabilitation history, a rehabilitation history in a convalescent rehabilitation hospital.

The model generation unit 103 generates a model that outputs, when information representing features of the target patient and a rehabilitation pattern are input, a result of predictions of physical ability values after the target patient performs rehabilitation indicated in this rehabilitation pattern. Specifically, this model is a model that predicts a physical ability value for each of a plurality of types of abilities. Specifically, the model outputs, for example, an evaluation value for each of evaluation items in the FIM. The model generation unit 103 trains the model by using pieces of past information and rehabilitation histories associated with the pieces of past information. More specifically, the model generation unit 103 trains the model by using, as training data, physical ability values after performing rehabilitation included in the past information, information about other features of the past patient included in the past information, and the rehabilitation history of the past patient associated with the past information. Note that the physical ability values after performing the rehabilitation are physical ability values after performing the rehabilitation indicated in the rehabilitation history used for the learning (i.e., the training). Further, the information about the other features is any other information included in the past information other than the physical ability values of the past patient after performing the rehabilitation, such as patient's attributes, the name of a disease, symptoms, physical ability values, and an individual target. For example, some or all of these information items may be used as information about other features for the learning process of the model. Data provided to the model has already been converted into numerically codes. For example, the model is a support vector machine (SVM: Support vector machine) or support vector regression (SVR: Support Vector Regression). However, the model is not limited to these examples, and may be other machine learning models such as a neural network.

The rehabilitation pattern selection unit 104 corresponds to the rehabilitation pattern selection unit 2 shown in FIG. 1, and selects one of a plurality of rehabilitation pattern candidates. The plurality of rehabilitation pattern candidates are candidates for rehabilitation patterns to be performed by the target patient. These candidates may be, for example, rehabilitation histories stored in the rehabilitation history storage unit 102, or combinations of contents of rehabilitation that differ from any of the rehabilitation histories stored in the rehabilitation history storage unit 102. In this example embodiment, in order to determine an appropriate rehabilitation pattern for a target patient, the evaluation of a rehabilitation pattern for this target patient is repeated. Therefore, the rehabilitation pattern selection unit 104 selects one of various rehabilitation patterns each time the evaluation is repeated. That is, the rehabilitation pattern selection unit 2 selects different rehabilitation patterns in repeated selection processes.

The ability value prediction unit 105 corresponds to the ability value prediction unit 3 shown in FIG. 1, and predicts physical ability values after the target patient performs rehabilitation indicated in a given rehabilitation pattern by using the model (i.e., the prediction model) generated by the model generation unit 103. The ability value prediction unit 105 inputs the rehabilitation pattern selected by the rehabilitation pattern selection unit 104 and the target patient information into the prediction model, and thereby predicts physical ability values after the target patient performs the rehabilitation indicated in the selected rehabilitation pattern. The target patient information input to the prediction model is information about the above-described other features that were used for the learning (i.e., the training) of the prediction model.

Note that when the past information of the past patient includes physical ability values after the discharge from the predetermined facility (specifically, for example, from the convalescent rehabilitation hospital), the ability value prediction unit 105 may estimate physical ability values of the target patient after the discharge. In such a case, the model generation unit 103 can train the model by using the physical ability values after the discharge.

Note that, for example, the target patient information is acquired as described below. For example, the therapist inputs target patient information to the terminal device 500, and the terminal device 500 transmits the input target patient information to the rehabilitation planning apparatus 100.

In this example embodiment, the same type of information as the past information is obtained as the target patient information. That is, in this example embodiment, similarly to the past information, the target patient information includes patient's attributes, the name of a disease, symptoms, physical ability values, an individual target, and the like. However, these information items are merely examples, and the target patient information is not limited to them. Note that the physical ability values included in the target patient information are, for example, information (e.g., time-series data) indicating temporal changes in the evaluation values in respective evaluation items in the FIM. As described above, the target patient information includes histories of physical ability values. In this example embodiment, the histories of physical ability values included in the target patient information includes at least histories of physical ability values in rehabilitation (acute-phase rehabilitation) performed in an acute-phase rehabilitation hospital. However, when the target patient has already performed rehabilitation (convalescent rehabilitation) in a convalescent rehabilitation hospital, the histories of physical ability values may further include histories of physical ability values in the rehabilitation (convalescent rehabilitation) in the convalescent rehabilitation hospital.

As described above, in this example embodiment, each of the pieces of past information and the target patient information includes histories of physical ability values for a predetermined rehabilitation period (specifically, for an acute-phase rehabilitation period). Further, at least the histories of physical ability values for the predetermined rehabilitation period are used for the leaning of the model and the prediction by the model. That is, the prediction model in this example embodiment is a model that has been trained in advance by using past information including histories of physical ability values, and the ability value prediction unit 105 inputs the selected rehabilitation pattern and the target patient information including histories of physical ability values into the prediction model. Note that changing patterns of physical ability values over a predetermined rehabilitation period may be used as histories of physical ability values used for the model. Histories (changing patterns) of physical ability values are an important element for determining patient's characteristics for rehabilitation. Therefore, it is possible to make a prediction more accurately by using histories (changing patterns) of physical ability values for rehabilitation as inputs to the model.

Further, in this example embodiment, each of the pieces of past information and the target patient information includes a target (an individual target) in rehabilitation. Further, at least this target is used for the leaning of the model and the prediction by the model. That is, the prediction model in this example embodiment is a model that has been trained in advance by using past information including a target, and the ability value prediction unit 105 inputs the selected rehabilitation pattern and the target patient information including the target into the prediction model. The target in rehabilitation is an important element for determining patient's characteristics for rehabilitation. Therefore, it is possible to make a prediction more accurately by using a target in rehabilitation as an input to the model.

Note that although histories of physical ability values for a predetermined rehabilitation period and a target in rehabilitation are used as inputs to the model in this example embodiment, only one of them may be used as an input to the model, or neither of them may be used as an input to the model.

The repetition control unit 106 corresponds to the repetition control unit 4 shown in FIG. 1, and performs control so as to repeat the selection by the rehabilitation pattern selection unit 104 and the prediction by the ability value prediction unit 105 until an end condition is satisfied. This end condition is an end condition for the evaluation of the rehabilitation pattern for the target patient, and specifically an arbitrary condition can be set as the end condition. For example, the end condition may be achievement of a predetermined number of repetitions, or a condition that a physical ability value output from the ability value prediction unit 105 should satisfy some criterion. For example, the repetition control unit 106 may perform control so as to finish the repetition when the degree of improvement of a physical ability value of the target patient output from the ability value prediction unit 105 from the current physical ability value thereof exceeds a predetermined threshold. Alternatively, the repetition control unit 106 may perform control so as to finish the repetition when the output of the ability value prediction unit 105 has converged.

A combination of a rehabilitation pattern and physical ability values is obtained each time the selection by the rehabilitation pattern selection unit 104 and the prediction by the ability value prediction unit 105 is repeated. That is, a combination of a rehabilitation pattern selected by the rehabilitation pattern selection unit 104 and physical ability values that are obtained by inputting this rehabilitation pattern into the prediction model is obtained.

The output control unit 107 includes the function of the determination unit 5 shown in FIG. 1. The output control unit 107 performs control so as to determine a rehabilitation pattern for, among the combinations of rehabilitation patterns and physical ability values obtained through the repetition process, a combination of which the physical ability value satisfies a predetermined condition as a rehabilitation plan for the target patient, and outputs the determined rehabilitation pattern (i.e., the rehabilitation plan). Specifically, the output control unit 107 performs control so as to output (i.e., to display) the rehabilitation pattern (i.e., the rehabilitation plan) on the display of the terminal device 500. Note that the predetermined condition is a condition indicating that the predicted physical ability value has a certain value. Therefore, for example, as the predetermined condition, any condition indicating that the predicted physical ability value of the target patient has improved from the current physical ability value thereof can be set. Specifically, this predetermined condition may be, for example, a condition that, when all the physical ability values obtained in the repetition process are ranked according to the degree of improvement, the physical ability value on which the decision is made should be in top k ranks (k is an integer equal to or greater than one) among all the physical ability values. In such a case, when k is two or greater, a plurality of rehabilitation patterns are output as the rehabilitation plan for the target patient. Further, for example, the predetermined condition may be a condition that the degree of improvement of the physical ability value on which the decision is made should be equal to or greater than a predetermined threshold. As described above, the output control unit 107 performs control so as to output, as a rehabilitation plan for the target patient, a rehabilitation pattern for which a result of a prediction that a physical ability value will improve is obtained. That is, the output control unit 107 recommends, as the rehabilitation plan for the target patient, the contents of rehabilitation by which the physical ability value will improve. As a result, the therapist can recognize (e.g., find) rehabilitation desirable for the target patient.

FIG. 3 is a schematic diagram showing an example of a rehabilitation plan displayed on the terminal device 500 under the control of the output control unit 107. As described above, the output control unit 107 outputs, as a rehabilitation plan, a rehabilitation pattern by which a prediction result that satisfies a predetermined condition is obtained (i.e., a rehabilitation pattern that was input to the prediction model when such a prediction result was output therefrom). Note that, in the example shown in FIG. 3, the rehabilitation pattern is a combination of contents of rehabilitation that are performed over a period from the first week after the admission to the convalescent rehabilitation hospital to the fourth week after the admission.

The ability value prediction unit 105 predicts a physical ability value for each of a plurality of types of abilities by using the prediction model. Therefore, as shown in FIG. 4, the output control unit 107 may perform control so as to output, along with the rehabilitation pattern, information for specifying the type of ability for which a prediction result indicating that the physical ability value will improve has been obtained. In the example shown in FIG. 4, it is shown that abilities to which upward arrows are added are those of which the ability values are predicted to improve. By clearly indicating abilities of which the ability values will improve as described above, it is possible to clearly indicate the reason for presenting the rehabilitation plan. Therefore, the therapist can determine the rehabilitation plan while knowing he/she can expect which abilities will improve.

Figure 5:
FIG. 5 is a schematic diagram showing an example of comparisons between physical ability values displayed on a terminal device under the control of an output control unit.

Further, the output control unit 107 may perform control so as to output, along with the rehabilitation pattern, a result of predictions of physical ability values after the target patient performs rehabilitation indicated in the rehabilitation pattern, obtained by the ability value prediction unit 105. FIG. 5 shows an example in which, in order to recognize the degree of improvement, current physical ability values of the target patient and physical ability values obtained as a result of predictions are compared with each other. More specifically, in the example shown in FIG. 5, physical ability values are compared for each of N types of physical abilities. Further, in the example shown in FIG. 5, the sum totals of physical ability values for certain abilities are compared with each other, and the sum totals of physical ability values for all the physical abilities are also compared with each other. Note that the N types of physical abilities are, for example, physical abilities defined in evaluation items in the FIM. Examples of the physical abilities include how well the patient can independently perform eating movements, and how well the patient can independently change his/her upper-body clothes.

Further, the output control unit 107 may also perform control so as to output other information along with the rehabilitation history. For example, the output control unit 107 may perform control so as to also output, by referring to a database or the like, incident information indicating incidents that occurred for past patients.

Figure 6:
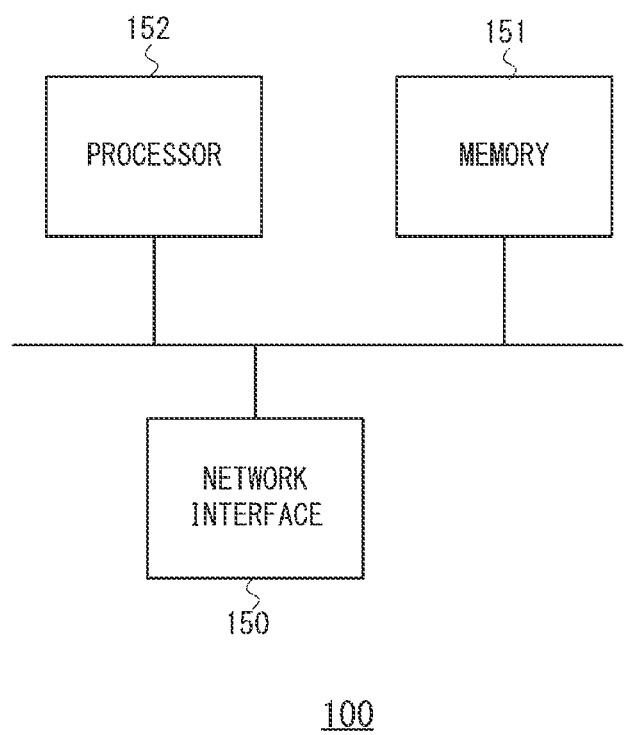
FIG. 6 is a schematic diagram showing an example of a hardware configuration of a rehabilitation planning apparatus according to the first example embodiment.

FIG. 6 is a schematic diagram showing an example of a hardware configuration of the rehabilitation planning apparatus 100. As shown in FIG. 6, the rehabilitation planning apparatus 100 includes a network interface 150, a memory 151, and a processor 152.

The network interface 150 is used to communicate with other arbitrary apparatus such as the terminal device 500. The memory 151 is composed of, for example, a combination of a volatile memory and a non-volatile memory. The memory 151 is used to store software (a computer program) including one or more instructions executed by the processor 152, and data (e.g., models) used for various processes performed by the rehabilitation planning apparatus 100. The past information storage unit 101 and the rehabilitation history storage unit 102 shown in FIG. 2 are implemented, for example, by the memory 151, but may instead be implemented by other storage devices.

The processor 152 performs a process performed by each of the components shown in FIG. 2 by loading the software (the computer program) from the memory 151 and executing the loaded software. That is, the process performed by each of the model generation unit 103, the rehabilitation pattern selection unit 104, the ability value prediction unit 105, the repetition control unit 106, and the output control unit 107 is performed, for example, by having the processor 152 execute the program. The processor 152 may be, for example, a microprocessor, an MPU (Micro Processor Unit), or a CPU (Central Processing Unit). The processor 152 may include a plurality of processors.

As described above, the rehabilitation planning apparatus 100 has functions as a computer. Note that, similarly, the terminal device 500 has a hardware configuration like the one shown in FIG. 6. That is, the processes performed by the terminal device 500 are implemented, for example, by having the processor execute the program.

Further, the program may be stored in various types of non-transitory computer readable media and thereby supplied to computers. The non-transitory computer readable media includes various types of tangible storage media. Examples of the non-transitory computer readable media include a magnetic recording medium (such as a flexible disk, a magnetic tape, and a hard disk drive), a magneto-optic recording medium (such as a magneto-optic disk), a CD-ROM (Read Only Memory), CD-R, CD-R/W, and a semiconductor memory (such as a mask ROM, a PROM (Programmable ROM), an EPROM (Erasable PROM), a flash ROM, and a RAM (Random Access Memory)). Further, the programs may be supplied to computers by using various types of transitory computer readable media. Examples of the transitory computer readable media include an electrical signal, an optical signal, and an electromagnetic wave. The transitory computer readable media can be used to supply programs to a computer through a wired communication line (e.g., electric wires and optical fibers) or a wireless communication line.

Figure 7:
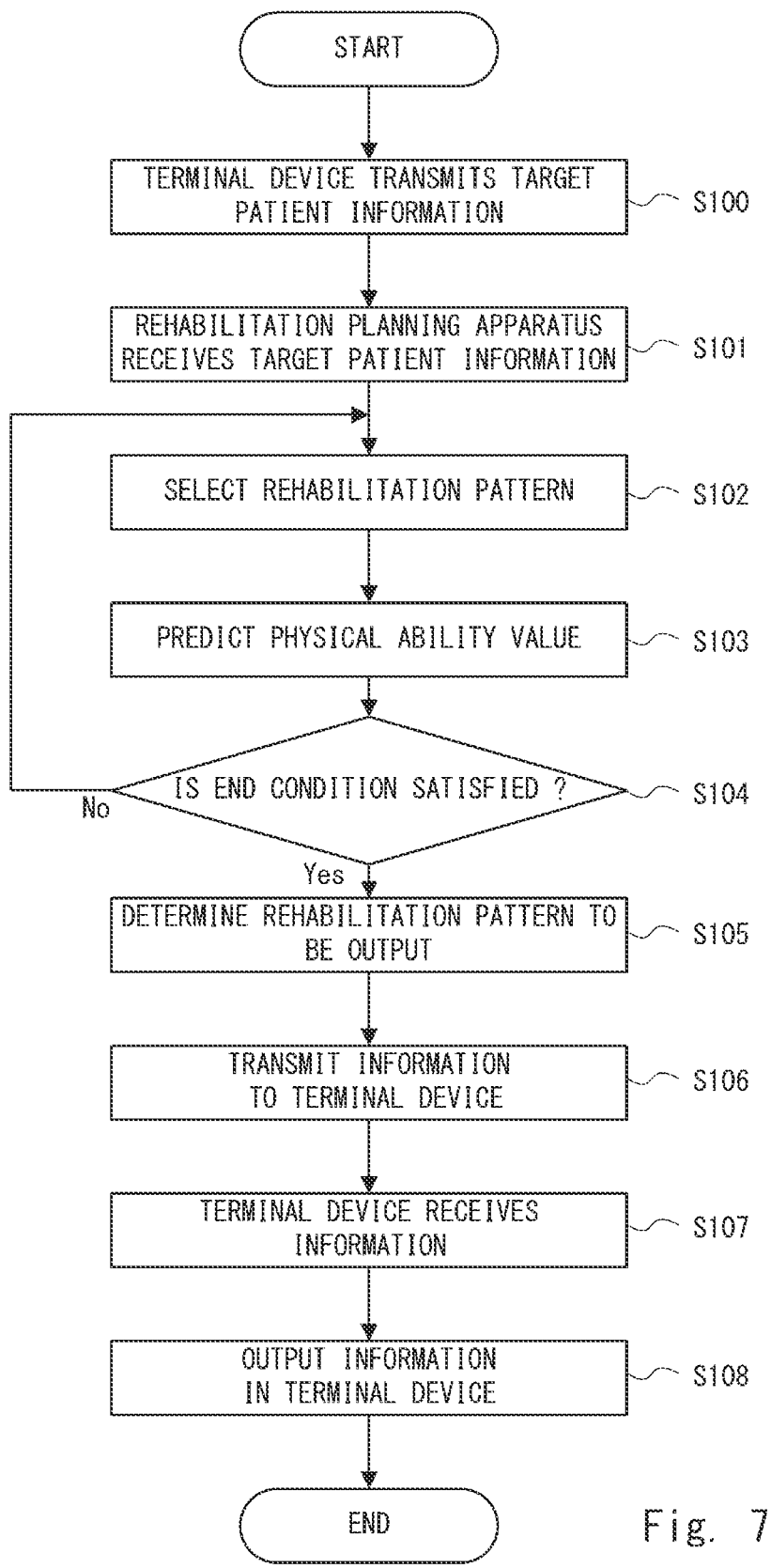
FIG. 7 is a flowchart showing an example of an output operation performed in the rehabilitation planning system according to the first example embodiment.

Next, a flow of operations performed by the rehabilitation planning system 10 will be described. FIG. 7 is a flowchart showing an example of an output operation performed in the rehabilitation planning system 10. Note that, prior to performing the processes in the flowchart shown in FIG. 7, a model has already been generated by the model generation unit 103. The flow of the output operation will be described hereinafter with reference to FIG. 7.

In a step S100, the terminal device 500 transmits target patient information to the rehabilitation planning apparatus 100.

Next, in a step S101, the rehabilitation planning apparatus 100 receives the target patient information. As a result, the rehabilitation planning apparatus 100 acquires the target patient information.

Next, in a step S102, the rehabilitation pattern selection unit 104 selects a rehabilitation pattern.

Next, in a step S103, the ability value prediction unit 105 predicts physical ability values by using the rehabilitation pattern selected in the step S102, the target patient information acquired in the step S101, and the prediction model.

Next, in a step S104, the repetition control unit 106 determines whether or not an end condition for the repetition has been satisfied. When the end condition for the repetition has not been satisfied yet, the process returns to the step S102 and another rehabilitation pattern is selected. On the other hand, when the end condition for the repetition has been satisfied, the process proceeds to a step S105.

In the step S105, the output control unit 107 determines a rehabilitation pattern to be output. That is, the output control unit 107 determines, as the rehabilitation pattern to be output, a rehabilitation pattern by which a predicted physical ability value(s) satisfies a predetermined condition(s).

Next, in a step S106, the output control unit 107 transmits the rehabilitation pattern which has been determined to be the rehabilitation pattern to be output in the step S105 to the terminal device 500. Note that, in the case when information other than the rehabilitation pattern is also output as described above, the output control unit 107 also transmits that information to the terminal device 500.

Next, in a step S107, the terminal device 500 receives the information.

Then, in a step S108, the terminal device 500 outputs the received information. Specifically, the terminal device 500 displays the received information, for example, on the display thereof.

The rehabilitation planning system 10 according to the first example embodiment has been described above. According to this system, a rehabilitation plan for a target patient is provided based on a result of a prediction by a model that has undergone a learning process by using information about past patients. Therefore, it is possible to efficiently create a rehabilitation plan. In particular, this system can determine s rehabilitation pattern to be output based on the predicted degree(s) of improvement of a physical ability value(s). Therefore, it is possible to present, to a therapist, a rehabilitation plan by which physical ability values can be improved. Therefore, for example, even a therapist with a small number of years of experience can make a rehabilitation plan by which physical ability values of a target patient can be improved. As a result, it is possible to reduce variations among the results (or effects) in regard to the recoveries of patients by therapists. Further, in this system, it is possible to present a rehabilitation plan by which physical ability value of a target patient can be improved. Therefore, it can also be expected to be effective to educate therapists who are not skilled in making appropriate rehabilitation plans by having them use this system.

Second Example Embodiment

Figure 8:
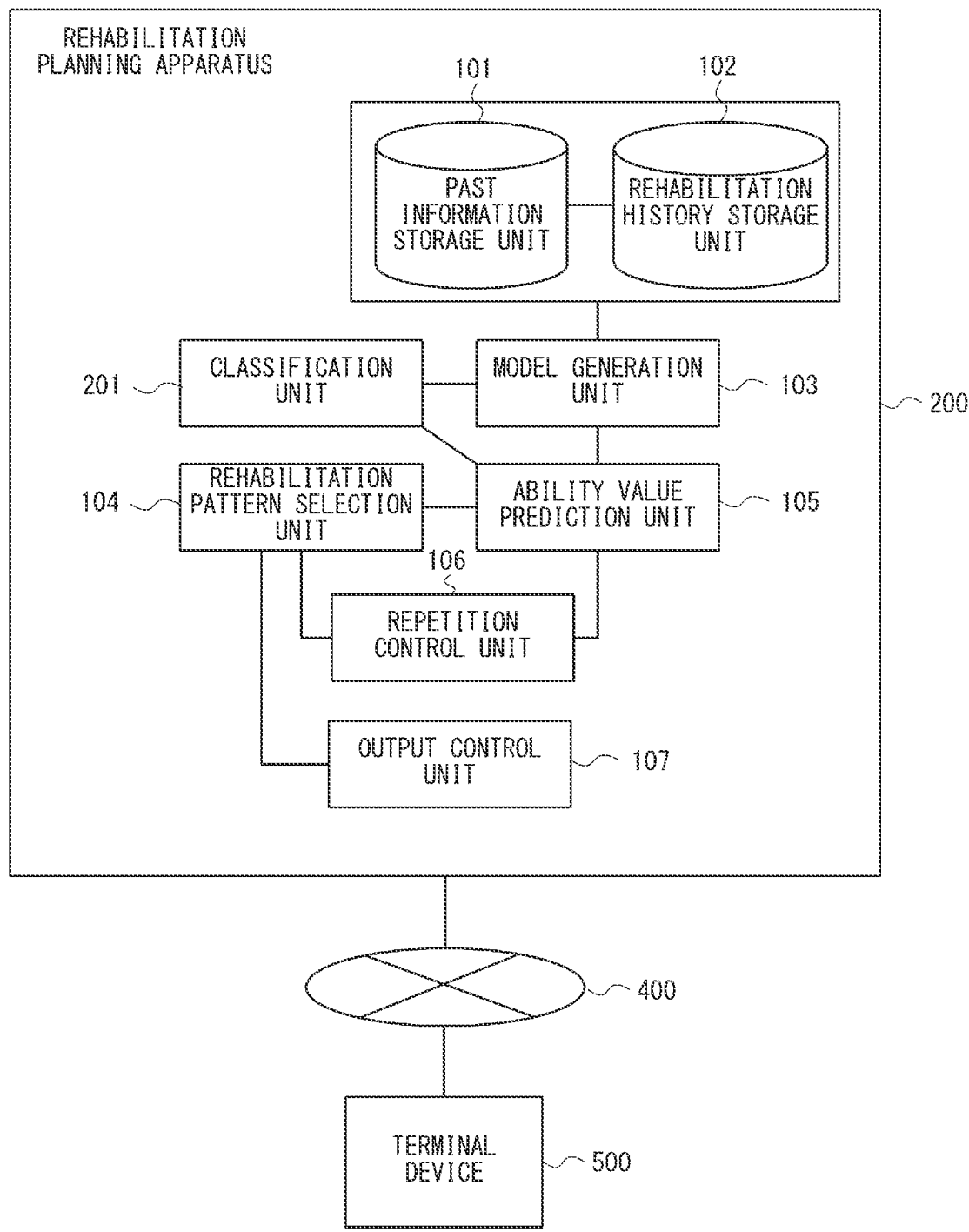
FIG. 8 is a block diagram showing an example of a configuration of a rehabilitation planning system according to a second example embodiment.

Next, a second example embodiment will be described. A rehabilitation planning system 20 according to a second example embodiment differs from the rehabilitation planning system 10 according to the first example embodiment in that the rehabilitation planning apparatus 100 is replaced by a rehabilitation planning apparatus 200. FIG. 8 is a block diagram showing an example of a configuration of the rehabilitation planning system 20 according to the second example embodiment. As shown in FIG. 8, the rehabilitation planning apparatus 200 differs from the rehabilitation planning apparatus 100 in the first example embodiment in that a classification unit 201 is added. Features that differ from those in the first example embodiment will be described hereinafter, while redundant descriptions will be omitted as appropriate. The process performed by the classification unit 201 is also processed, for example, by having the processor 152 load the software (the computer program) from the memory 151 and execute the loaded software.

The classification unit 201 classifies pieces of past information and target patient information based on information included in the pieces of past information and in the target patient information. In the first example embodiment, the model generation unit 103 generates one model for predicting physical ability values by using past information stored in the past information storage unit 101. In other words, in the first example embodiment, physical ability values of all the target patients are predicted by using one prediction model. When there is a patient(s) whose characteristics are significantly differ from those of the target patient among the past patients used in the learning process for the model, an appropriate model may not be obtained. Therefore, in this example embodiment, by classifying pieces of past information and target patient information while focusing on information (items) included in the pieces of past information and the target patient information, a model by which a more accurate prediction can be made than in the case where such classification is not performed is generated. Note that, for example, histories of physical ability values may be used as information used for the classification. More specifically, the pieces of past information and the target patient information may be classified based on changing patterns of physical ability value during a predetermined rehabilitation period (e.g., a period during which acute-phase rehabilitation was performed). Further, targets (individual targets) for rehabilitation may be used as the information used for the classification. However, they are merely examples, and the pieces of past information and the target patient information may be classified based on other information included in the past information and in the target patient information.

The classification unit 201 classifies pieces of past information and target patient information based on information included in the pieces of past information and in the target patient information. Specifically, the classification unit 201 performs a clustering process for the pieces of past information and the target patient information while focusing on the aforementioned information, and thereby classifies each of the pieces of past information and the target patient information into one of categories.

The model generation unit 103 in this example embodiment generates a model for each of the classified categories. That is, the model generation unit 103 generates a model by using pieces of past information classified in the same category and rehabilitation histories of past patients associated with these pieces of past information. Therefore, in this example embodiment, the model generation unit 103 generates a plurality of models according to the number of categories (i.e., generates as many models as the number of categories).

Further, the ability value prediction unit 105 makes a prediction by using, among the generated prediction models, a prediction model that has undergone a learning process by using pieces of past information classified in the category in which the target patient information has been classified and rehabilitation histories associated with these pieces of past information.

Figure 9:
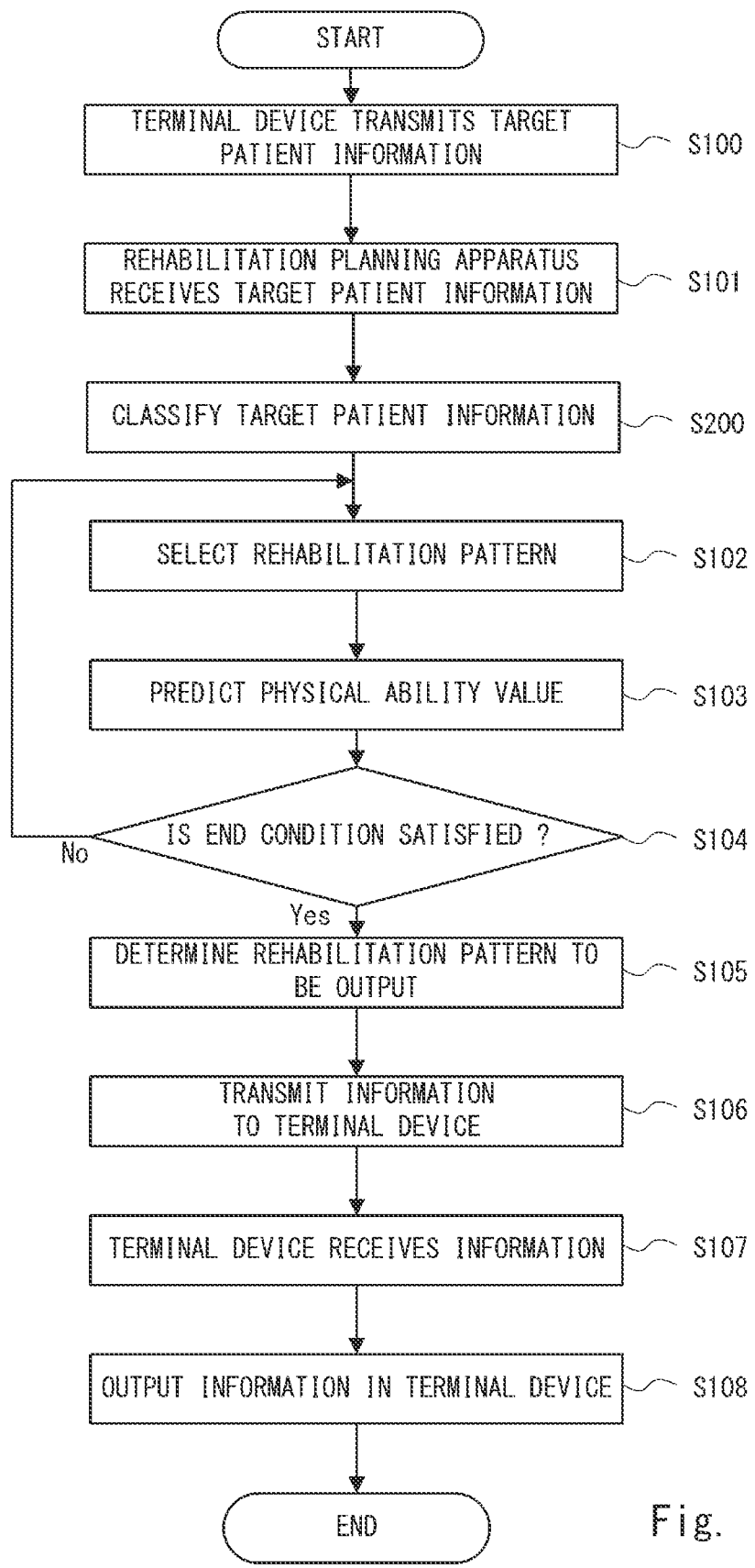
FIG. 9 is a flowchart showing an example of an output operation performed in the rehabilitation planning system according to the second example embodiment.

FIG. 9 is a flowchart showing an example of an output operation performed in the rehabilitation planning system 20. Note that, prior to performing the processes in the flowchart shown in FIG. 9, pieces of past information have already been classified by the classification unit 201 and a model has already been generated using the classified pieces of past information by the model generation unit 103. The flowchart shown in FIG. 9 differs from that shown in FIG. 7 in that a step S200 indicating the process performed by the classification unit 201 is added. Features that differ from those shown in FIG. 7 will be described hereinafter, while descriptions of the same features as those shown in FIG. 7 will be omitted as appropriate.

In the flowchart shown in FIG. 9, the process proceeds to a step S200 after the process in the step S101.

In the step S200, the classification unit 201 performs a clustering process for the target patient information received in the step S101, and thereby classifies the target patient information. Based on this classification, the ability value prediction unit 105 determines a prediction model that will be applied to the target patient information. That is, the ability value prediction unit 105 determines to use a prediction model which is based on the pieces of past information classified in the category in which the target patient information has been classified.

Next, the process proceeds to a step S102 after the step S200, and a rehabilitation pattern is selected. Then, in a step S103, the ability value prediction unit 105 predicts physical ability values by using the prediction model corresponding to the category in which the target patient information has been categorized.

After that, processes similar to those in FIG. 7 are performed.

The second example embodiment has been described above. In this example embodiment, a process is performed by the classification unit 201 and an appropriate model is selected according to the target patient. Therefore, a more accurate prediction can be made than in the case where the above-described classification is not performed.

Third Example Embodiment

Figure 10:
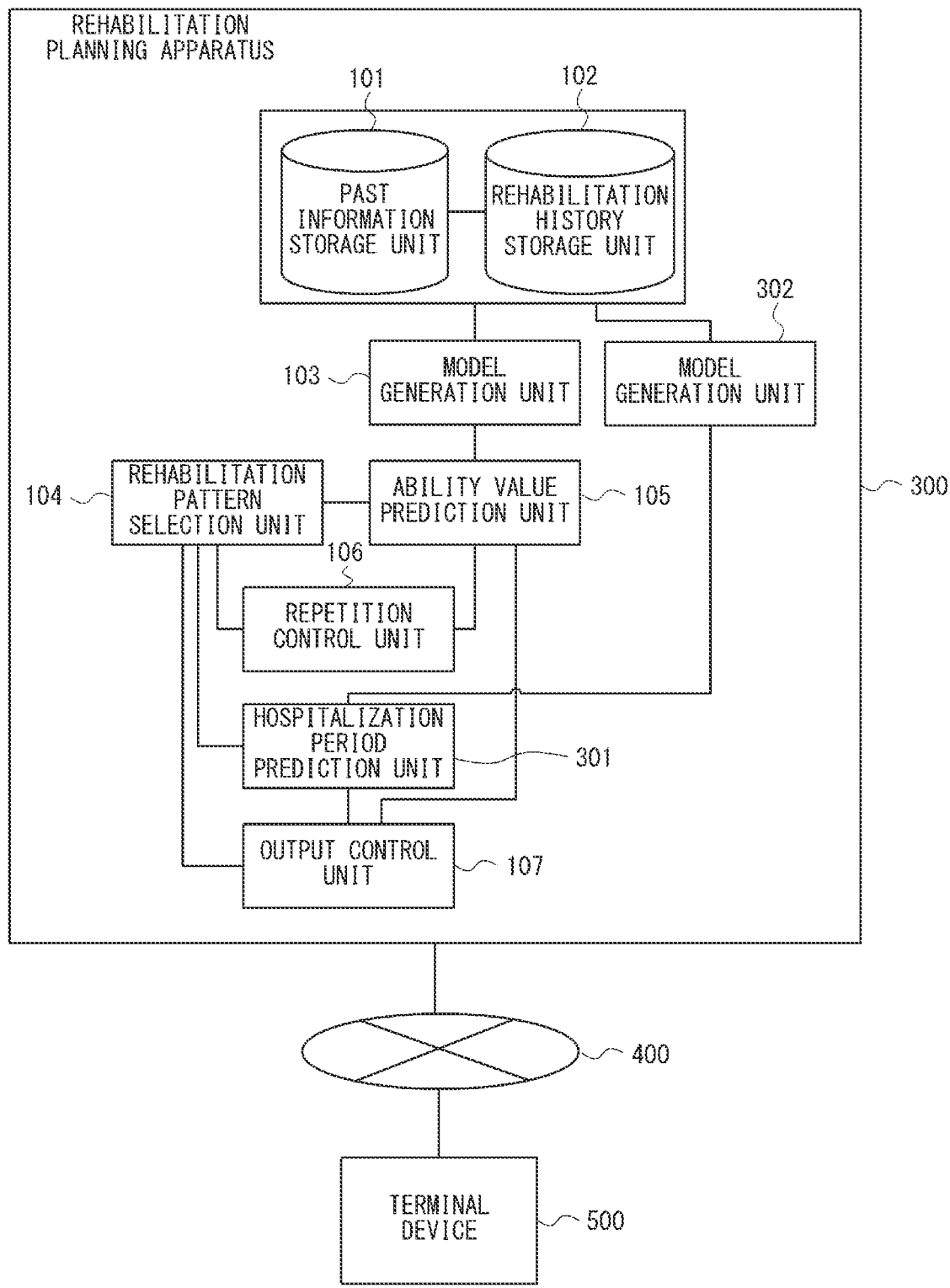
FIG. 10 is a block diagram showing an example of a configuration of a rehabilitation planning system according to a third example embodiment.

Next, a third example embodiment will be described. A rehabilitation planning system 30 according to a third example embodiment differs from the rehabilitation planning system 10 according to the first example embodiment in that the rehabilitation planning apparatus 100 is replaced by a rehabilitation planning apparatus 300. FIG. 10 is a block diagram showing an example of a configuration of the rehabilitation planning system 30 according to the third example embodiment. As shown in FIG. 10, the rehabilitation planning apparatus 300 differs from the rehabilitation planning apparatus 100 according to the first example embodiment in that a hospitalization period prediction unit 301 and a model generation unit 302 are added. The process performed by each of the hospitalization period prediction unit 301 and the model generation unit 302 is also processed, for example, by having the processor 152 load the software (the computer program) from the memory 151 and execute the loaded software. Features that differ from those in the first example embodiment will be described hereinafter, while redundant descriptions will be omitted as appropriate. Note that the following description will be given under the assumption that the past information of a past patient includes his/her hospitalization period in a predetermined facility (specifically, for example, in a convalescent rehabilitation hospital).

The hospitalization period prediction unit 301 predicts a hospitalization period in a predetermined facility (or a predetermined institution) (specifically, for example, in a convalescent rehabilitation hospital) on the assumption that the target patient performs rehabilitation indicated in the rehabilitation pattern by using a prediction model that has undergone a learning process in advance.

The model generation unit 302 generates a model that will be used by the hospitalization period prediction unit 301. The model generation unit 302 generates a model that, when information representing features of the target patient and a rehabilitation pattern are input, outputs a result of a prediction of a hospitalization period on the assumption that the target patient performs rehabilitation indicated in this rehabilitation pattern. The model generation unit 302 trains the model by using pieces of past information and rehabilitation histories associated with the pieces of past information. More specifically, the model generation unit 302 trains the model by using, as training data, hospitalization periods of past patients included in the past information, information about other features of the past patients included in the past information, and rehabilitation histories of the past patients associated with the pieces of past information. Note that the information about the other features is any other information included in the past information other than the hospitalization period of the past patient, such as patient's attributes, the name of a disease, symptoms, physical ability values, and an individual target. For example, some or all of these information items may be used as information about other features for the learning process of the model. Data provided to the model has already been converted into numerically codes. For example, the model is a support vector machine or support vector regression. However, the model is not limited to these examples, and may be other machine learning models such as a neural network.

The hospitalization period prediction unit 301 predicts a hospitalization period on the assumption that the target patient performs rehabilitation indicated in a given rehabilitation pattern by using the model (i.e., the prediction model) generated by the model generation unit 302. The hospitalization period prediction unit 301 inputs the rehabilitation pattern selected by the rehabilitation pattern selection unit 104 and the target patient information into the prediction model, and thereby predicts a hospitalization period on the assumption that the target patient performs rehabilitation indicated in the selected rehabilitation pattern. The target patient information input to the prediction model is information about the above-described other features that were used for the learning (i.e., the training) of the prediction model.

The output control unit 107 in this example embodiment performs control so as to output the predicted hospitalization period along with the rehabilitation pattern.

Figure 11:
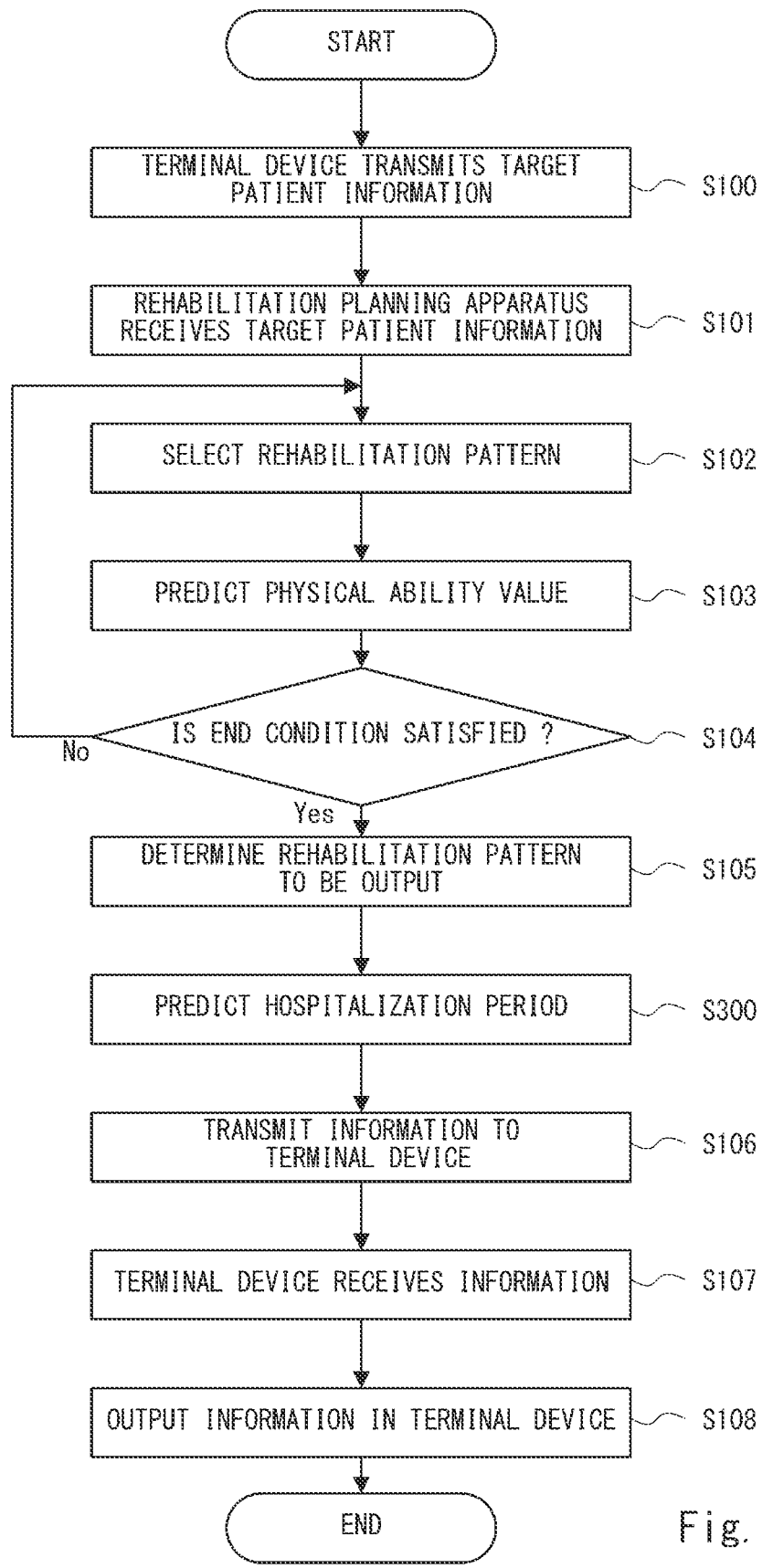
FIG. 11 is a flowchart showing an example of an output operation performed in the rehabilitation planning system according to the third example embodiment.

FIG. 11 is a flowchart showing an example of an output operation performed in the rehabilitation planning system 30. Note that, prior to performing the processes in the flowchart shown in FIG. 11, models have already been generated by the model generation unit 103 and the model generation unit 302. The flowchart shown in FIG. 11 differs from that shown in FIG. 7 in that a step S300 indicating the process performed by the hospitalization period prediction unit 301 is added. Features that differ from those shown in FIG. 7 will be described hereinafter, while descriptions of the same features as those shown in FIG. 7 will be omitted as appropriate.

In the flowchart shown in FIG. 11, after the processes from steps S100 to S105 are performed, the process proceeds to a step S300.

In the step S300, the hospitalization period prediction unit 301 predicts a hospitalization period by using the rehabilitation pattern determined to be the rehabilitation pattern to be output in the step S105, the target patient information acquired in the step S101, and the prediction model generated by the model generation unit 302. The result of the prediction by the hospitalization period prediction unit 301 is transmitted, as information to be output, to the terminal device 500.

The process proceeds to a step S106 after the process in the step S300. That is, after the step S300, the processes in the step S106 and the subsequent steps are performed in a manner similar to that shown in FIG. 7.

The third example embodiment has been described above. In this example embodiment, a result of a prediction of a hospitalization period that is made on the assumption that the target patient performs rehabilitation is output. Therefore, it is possible to provide more useful information when creating a rehabilitation plan.

Note that the classification unit 201 shown in the second example embodiment may also be added in this example embodiment. That is, in this example embodiment, the model generation unit 103 may also generate a model for each classified category, and the ability value prediction unit 105 may also make a prediction by using a prediction model which is based on pieces of past information classified in the category in which the target patient information has been classified.

Further, the result of the classification by the classification unit 201 may also be used for the prediction of a hospitalization period. That is, the model generation unit 302 may generate a model for each classified category, and the hospitalization period prediction unit 301 may make a prediction by using a prediction model which is based on pieces of past information classified in the category in which the target patient information has been classified. In this way, a hospitalization period can also be predicted more accurately than in the case where the above-described classification is not performed.

Note that the present invention is not limited to the above-described example embodiments and various modifications can be made within the scope and spirit of the invention.

Further, the whole or part of the example embodiments disclosed above can be described as, but not limited to, the following supplementary notes.

(Supplementary Note 1)

A rehabilitation planning apparatus comprising:
  rehabilitation pattern selection means for selecting one of a plurality of rehabilitation pattern candidates;
  ability value prediction means for predicting a physical ability value after a target patient performs rehabilitation indicated in the selected rehabilitation pattern based on the selected rehabilitation pattern and target patient information by using a prediction model, the target patient information being information about the target patient;
  repetition control means for controlling a repetition of a selection of a different rehabilitation pattern by the rehabilitation pattern selection means and a prediction corresponding to this rehabilitation pattern by the ability value prediction means; and
  determination means for determining a rehabilitation pattern for, among combinations of rehabilitation patterns and physical ability values obtained through the repetition of the selection by the rehabilitation pattern selection means and the prediction by the ability value prediction means, a combination of which the physical ability value satisfies a predetermined condition as a rehabilitation plan for the target patient, wherein
  the prediction model is a model that has undergone a learning process in advance by using a plurality of pieces of past information and rehabilitation histories, each of the plurality of pieces of past information being information about a respective one of a plurality of past patients who performed rehabilitation in a past, and the rehabilitation histories being rehabilitation histories of the past patients associated with the pieces of past information.

(Supplementary Note 2)

The rehabilitation planning apparatus described in Supplementary note 1, wherein
  each of the pieces of past information and the target patient information includes a history of a physical ability value for a predetermined rehabilitation period,
  the prediction model is a model that has undergone a learning process in advance by using the past information including the history of the physical ability value, and
  the ability value prediction means inputs the selected rehabilitation pattern and the target patient information including the history of the physical ability value to the prediction model.

(Supplementary Note 3)

The rehabilitation planning apparatus described in Supplementary note 1 or 2, wherein
  each of the pieces of past information and the target patient information includes a target in rehabilitation, the prediction model is a model that has undergone a learning process in advance by using the past information including the target, and the ability value prediction means inputs the selected rehabilitation pattern and the target patient information including the target to the prediction model.

(Supplementary Note 4)

The rehabilitation planning apparatus described in any one of Supplementary notes 1 to 3, wherein the ability value prediction means makes a prediction by using the prediction model that has undergone a learning process in advance by using pieces of past information and rehabilitation histories of past patients associated with the pieces of past information, the pieces of past information being those that are classified, based on information included in the pieces of past information and the target patient information, in a category in which the target patient information has been classified.

(Supplementary Note 5)

The rehabilitation planning apparatus described in Supplementary note 4, wherein each of the pieces of past information and the target patient information includes a history of a physical ability value for a predetermined rehabilitation period, and the information used for the classification is the history of the physical ability value.

(Supplementary Note 6)

The rehabilitation planning apparatus described in Supplementary note 4, wherein each of the pieces of past information and the target patient information includes a target in rehabilitation, and the information used for the classification is a target in the rehabilitation.

(Supplementary Note 7)

The rehabilitation planning apparatus described in any one of Supplementary notes 1 to 6, wherein the ability value prediction means predicts a physical ability value for each of a plurality of types of abilities.

(Supplementary Note 8)

The rehabilitation planning apparatus described in any one of Supplementary notes 1 to 7, further comprising hospitalization period prediction means for predicting, by using a prediction model that has undergone a learning process in advance, a hospitalization period on an assumption that the target patient performs rehabilitation indicated in the rehabilitation pattern.

(Supplementary Note 9)

A rehabilitation planning system comprising a rehabilitation planning apparatus, and a terminal device, wherein the rehabilitation planning apparatus comprises:

rehabilitation pattern selection means for selecting one of a plurality of rehabilitation pattern candidates;

ability value prediction means for predicting a physical ability value after a target patient performs rehabilitation indicated in the selected rehabilitation pattern based on the selected rehabilitation pattern and target patient information by using a prediction model, the target patient information being information about the target patient input from the terminal device;

repetition control means for controlling a repetition of a selection of a different rehabilitation pattern by the rehabilitation pattern selection means and a prediction corresponding to this rehabilitation pattern by the ability value prediction means; and output control means for preforming control so as to output a rehabilitation pattern for, among combinations of rehabilitation patterns and physical ability values obtained through the repetition of the selection by the rehabilitation pattern selection means and the prediction by the ability value prediction means, a combination of which the physical ability value satisfies a predetermined condition as a rehabilitation plan for the target patient to the terminal device, and the prediction model is a model that has undergone a learning process in advance by using a plurality of pieces of past information and rehabilitation histories, each of the plurality of pieces of past information being information about a respective one of a plurality of past patients who performed rehabilitation in a past, and the rehabilitation histories being rehabilitation histories of the past patients associated with the pieces of past information.

(Supplementary Note 10)

The rehabilitation planning system described in Supplementary note 9, wherein each of the pieces of past information and the target patient information includes a history of a physical ability value for a predetermined rehabilitation period, the prediction model is a model that has undergone a learning process in advance by using the past information including the history of the physical ability value, and the ability value prediction means inputs the selected rehabilitation pattern and the target patient information including the history of the physical ability value to the prediction model.

(Supplementary Note 11)

The rehabilitation planning system described in Supplementary note 9 or 10, wherein the ability value prediction means predicts a physical ability value for each of a plurality of types of abilities, and the output control unit performs control so as to output, along with the rehabilitation pattern, information for specifying a type of ability for which a prediction result indicating that a physical ability value will improve has been obtained.

(Supplementary Note 12)

The rehabilitation planning system described in any one of Supplementary notes 9 to 11, further comprising hospitalization period prediction means for predicting, by using a prediction model that has undergone a learning process in advance, a hospitalization period on an assumption that the target patient performs rehabilitation indicated in the rehabilitation pattern, wherein the output control means performs control so as to output the predicted hospitalization period along with the rehabilitation pattern.

(Supplementary Note 13)

The rehabilitation planning system described in any one of Supplementary notes 9 to 12, wherein the output control means performs control so as to output, along with the rehabilitation pattern, a result of a prediction of a physical ability value after the target patient performs rehabilitation indicated in the rehabilitation pattern, predicted by the ability value prediction means.

(Supplementary Note 14)

A rehabilitation planning method comprising:

selecting one of a plurality of rehabilitation pattern candidates;

predicting a physical ability value after a target patient performs rehabilitation indicated in the selected rehabilitation pattern based on the selected rehabilitation pattern and target patient information by using a prediction model, the target patient information being information about the target patient;

controlling a repetition of a selection of a different rehabilitation pattern and a prediction corresponding to this rehabilitation pattern; and determining a rehabilitation pattern for, among combinations of rehabilitation patterns and physical ability values obtained through the repetition of the selection and the prediction, a combination of which the physical ability value satisfies a predetermined condition as a rehabilitation plan for the target patient, wherein the prediction model is a model that has undergone a learning process in advance by using a plurality of pieces of past information and rehabilitation histories, each of the plurality of pieces of past information being information about a respective one of a plurality of past patients who performed rehabilitation in a past, and the rehabilitation histories being rehabilitation histories of the past patients associated with the pieces of past information.

(Supplementary Note 15)

A non-transitory computer readable medium storing a program for causing a computer to perform:

a rehabilitation pattern selection step for selecting one of a plurality of rehabilitation pattern candidates;

an ability value prediction step of predicting a physical ability value after a target patient performs rehabilitation indicated in the selected rehabilitation pattern based on the selected rehabilitation pattern and target patient information by using a prediction model, the target patient information being information about the target patient;

a repetition control step of controlling a repetition of a selection of a different rehabilitation pattern and a prediction corresponding to this rehabilitation pattern; and a determination step of determining a rehabilitation pattern for, among combinations of rehabilitation patterns and physical ability values obtained through the repetition of the selection in the rehabilitation pattern selection step and the prediction in the ability value prediction step, a combination of which the physical ability value satisfies a predetermined condition as a rehabilitation plan for the target patient, wherein the prediction model is a model that has undergone a learning process in advance by using a plurality of pieces of past information and rehabilitation histories, each of the plurality of pieces of past information being information about a respective one of a plurality of past patients who performed rehabilitation in a past, and the rehabilitation histories being rehabilitation histories of the past patients associated with the pieces of past information.

Although the present invention is described above with reference to example embodiments, the present invention is not limited to the above-described example embodiments. Various modifications that can be understood by those skilled in the art can be made to the configuration and details of the present invention within the scope of the invention.

This application is based upon and claims the benefit of priority from Japanese patent application No. 2019-184153, filed on Oct. 4, 2019, the disclosure of which is incorporated herein in its entirety by reference.

REFERENCE SIGNS LIST

1 REHABILITATION PLANNING APPARATUS
2 REHABILITATION PATTERN SELECTION UNIT
3 ABILITY VALUE PREDICTION UNIT
4 REPETITION CONTROL UNIT
5 DETERMINATION UNIT
10 REHABILITATION PLANNING SYSTEM
20 REHABILITATION PLANNING SYSTEM
30 REHABILITATION PLANNING SYSTEM
100 REHABILITATION PLANNING APPARATUS
101 PAST INFORMATION STORAGE UNIT
102 REHABILITATION HISTORY STORAGE UNIT
103 MODEL GENERATION UNIT
104 REHABILITATION PATTERN SELECTION UNIT
105 ABILITY VALUE PREDICTION UNIT
106 REPETITION CONTROL UNIT
107 OUTPUT CONTROL UNIT
150 NETWORK INTERFACE
151 MEMORY
152 PROCESSOR
200 REHABILITATION PLANNING APPARATUS
201 CLASSIFICATION UNIT
300 REHABILITATION PLANNING APPARATUS
301 HOSPITALIZATION PERIOD PREDICTION UNIT
302 MODEL GENERATION UNIT
400 NETWORK
500 TERMINAL DEVICE

What is claimed is:

1. A rehabilitation planning apparatus comprising:

at least one memory storing program instructions; and at least one processor configured to execute the program instructions stored in the memory to:

train a prediction model in advance, the prediction model trained to output, based on an input rehabilitation pattern and input patient information, a predicted physical ability value for each of a plurality of ability types after a patient having the input patient information performs the input rehabilitation pattern, wherein the prediction model is a support vector machine, a support vector regression model, or a neural network, the prediction model is trained by using a plurality of pieces of patient information respectively regarding a plurality of past patients who previously have performed rehabilitation, and by using rehabilitation histories of the past patients associated with the pieces of past information, each piece of patient information includes a name of a disease that a corresponding past patient has, symptoms that the corresponding past patient has, and attributes of the corresponding past patient including at least age and gender, and the rehabilitation history of each past patient includes a past rehabilitation pattern or patterns that the each past patient performed and a resulting physical ability value;

for each of a plurality of times, select a rehabilitation pattern and predict a physical ability value of the selected rehabilitation pattern for each of the plurality of ability types, wherein for each time, the rehabilitation pattern is selected from among a plurality of rehabilitation pattern candidates, the physical ability value of the rehabilitation pattern for each of the plurality of ability types is indicative of a physical ability of a target patient after the target patient performs rehabilitation indicated by the selected rehabilitation pattern, the physical ability value for each of the plurality of ability types is predicted by using the prediction model, based on the selected rehabilitation pattern and based on target patient information regarding the target patient, and the target patient information includes a name of a disease that the target patient has, symptoms that the target patient has, and attributes of the target patient including at least age and gender;

determine a plurality of combinations of the rehabilitation patterns;

determine, from among the combinations, a combination of the rehabilitation patterns for which the physical ability values satisfy a predetermined condition, as a rehabilitation plan for the target patient; and output, along with the rehabilitation plan for the target patient, a mark for specifying the ability type for which the physical ability value will improve after the target patient has performed the rehabilitation plan.

2. The rehabilitation planning apparatus according to claim 1, wherein each piece of patient information and the target patient information includes a history of the physical ability value for a predetermined rehabilitation period, for each of the plurality of ability types, the prediction model is trained by further using the history of the physical ability value of each piece of patient information for each of the plurality of ability types, and the physical ability for each of the plurality of ability types is predicted by using the prediction model based further on the history of the physical ability value of the target patient information for each of the plurality of ability types.

3. The rehabilitation planning apparatus according to claim 1, wherein each piece of patient information and the target patient information includes a target in rehabilitation, the prediction model is trained by further using the target in rehabilitation of each piece of patent information, and the physical ability for each of the plurality of ability types is predicted by using the prediction model based further on the target in rehabilitation of the target patient information.

4. The rehabilitation planning apparatus according to claim 1, wherein the pieces of patient information are those that have been classified in a category in which the target patient information has been classified.

5. The rehabilitation planning apparatus according to claim 4, wherein each piece of patient information and the target patient information includes a history of the physical ability value for a predetermined rehabilitation period, for each of the plurality of ability types, and each piece of patient information and the target patient information is classified based on the history of the physical ability value for each of the plurality of ability types.

6. The rehabilitation planning apparatus according to claim 4, wherein each piece of patient information and the target patient information includes a target in rehabilitation, and each piece of patient information and the target patient information is classified based on the target in rehabilitation.

7. The rehabilitation planning apparatus according to claim 1, wherein the at least one processor is further configured to execute the program instructions to predict, by using the prediction model, a hospitalization period on an assumption that the target patient performs rehabilitation indicated in the selected rehabilitation pattern.

8. The rehabilitation planning apparatus according to claim 1, wherein the at least one processor is further configured to execution the program instructions to output, to a terminal device of a therapist, the rehabilitation plan to support decision-making by the therapist regarding to generation of the rehabilitation plan.

9. A rehabilitation planning method performed by a computer and comprising:

training a prediction model in advance, the prediction model trained to output, based on an input rehabilitation pattern and input patient information, a predicted physical ability value for each of a plurality of ability types after a patient having the input patient information performs the input rehabilitation pattern, wherein the prediction model is a support vector machine, a support vector regression model, or a neural network, the prediction model is trained by using a plurality of pieces of patient information respectively regarding a plurality of past patients who previously have performed rehabilitation, and by using rehabilitation histories of the past patients associated with the pieces of past information, each piece of patient information includes a name of a disease that a corresponding past patient has, symptoms that the corresponding past patient has, and attributes of the corresponding past patient including at least age and gender, and the rehabilitation history of each past patient includes a past rehabilitation pattern or patterns that the each past patient performed and a resulting physical ability value;

for each of a plurality of times, selecting a rehabilitation pattern and predicting a physical ability value of the selected rehabilitation pattern for each of the plurality of ability types, wherein for each time, the rehabilitation pattern is selected from among a plurality of rehabilitation pattern candidates, the physical ability value of the rehabilitation pattern for each of the plurality of ability types is indicative of a physical ability of a target patient after the target patient performs rehabilitation indicated by the selected rehabilitation pattern, the physical ability value for each of the plurality of ability types is predicted by using the prediction model, based on the selected rehabilitation pattern and based on target patient information regarding the target patient, and the target patient information includes a name of a disease that the target patient has, symptoms that the target patient has, and attributes of the target patient including at least age and gender;

determining a plurality of combinations of the rehabilitation patterns;

determining, from among the combinations, a combination of the rehabilitation patterns for which the physical ability values satisfy a predetermined condition, as a rehabilitation plan for the target patient; and outputting, along with the rehabilitation plan for the target patient, a mark for specifying the ability type for which the physical ability value will improve after the target patient has performed the rehabilitation plan.

10. A non-transitory computer readable medium storing a program executable by a computer to perform processing comprising:

training a prediction model in advance, the prediction model trained to output, based on an input rehabilitation pattern and input patient information, a predicted physical ability value for each of a plurality of ability types after a patient having the input patient information performs the input rehabilitation pattern, wherein the prediction model is a support vector machine, a support vector regression model, or a neural network, the prediction model is trained by using a plurality of pieces of patient information respectively regarding a plurality of past patients who previously have performed rehabilitation, and by using rehabilitation histories of the past patients associated with the pieces of past information, each piece of patient information includes a name of a disease that a corresponding past patient has, symptoms that the corresponding past patient has, and attributes of the corresponding past patient including at least age and gender, and the rehabilitation history of each past patient includes a past rehabilitation pattern or patterns that the each past patient performed and a resulting physical ability value;

for each of a plurality of times, selecting a rehabilitation pattern and predicting a physical ability value of the selected rehabilitation pattern for each of the plurality of ability types, wherein for each time, the rehabilitation pattern is selected from among a plurality of rehabilitation pattern candidates, the physical ability value of the rehabilitation pattern for each of the plurality of ability types is indicative of a physical ability of a target patient after the target patient performs rehabilitation indicated by the selected rehabilitation pattern, the physical ability value for each of the plurality of ability types is predicted by using the prediction model, based on the selected rehabilitation pattern and based on target patient information regarding the target patient, and the target patient information includes a name of a disease that the target patient has, symptoms that the target patient has, and attributes of the target patient including at least age and gender;

determining a plurality of combinations of the rehabilitation patterns;

determining, from among the combinations, a combination of the rehabilitation patterns for which the physical ability values satisfy a predetermined condition, as a rehabilitation plan for the target patient; and outputting, along with the rehabilitation plan for the target patient, a mark for specifying the ability type for which the physical ability value will improve after the target patient has performed the rehabilitation plan.

\* \* \* \* \*